United States Patent [19]

Clayton

[11] Patent Number: 4,534,968
[45] Date of Patent: Aug. 13, 1985

[54] PHARMACEUTICAL COMPOSITIONS

[75] Inventor: John P. Clayton, Horsham, England

[73] Assignee: Beecham Group Limited, England

[21] Appl. No.: 163,230

[22] Filed: Jun. 26, 1980

Related U.S. Application Data

[63] Continuation of Ser. No. 887,843, Mar. 17, 1978, abandoned, which is a continuation of Ser. No. 804,998, Jun. 9, 1977, abandoned.

[30] Foreign Application Priority Data

Jun. 26, 1976 [GB] United Kingdom ............. 26689/76

[51] Int. Cl.$^3$ .............................................. A61K 35/00
[52] U.S. Cl. .................................................. 424/114
[58] Field of Search ......................................... 424/114

[56] References Cited

PUBLICATIONS

Chemical Abstracts 77: 126629v, (1972).
Chemical Abstracts 81: 63616y, (1974).
Derwent Farm Doc. #72840/w/44/, Abstracting DT 2517316, published 10/23/75.

Primary Examiner—Jerome D. Goldberg
Attorney, Agent, or Firm—Jacobs & Jacobs

[57] ABSTRACT

A synergistic combination is produced which comprises a synergistically effective amount of clavulanic acid or a pharmaceutically acceptable salt thereof and an antibacterially effective amount of a compound of the formula (II):

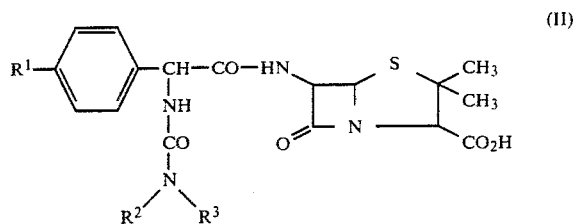

or a pharmaceutically acceptable salt thereof wherein $R^1$ is hydrogen, hydroxyl or acetoxyl, $R^2$ is methyl and $R^3$ is $CO.R^4$ wherein $R^4$ is phenyl, isobutyl, furyl, thienyl or $NHCH_3$ or $R^2$ is joined to $R^3$ so that $NR^2R^3$ is an imidazolin-2-on-1-yl.

33 Claims, No Drawings

PHARMACEUTICAL COMPOSITIONS

CROSS-REFERENCE

This is a continuation of Ser. No. 887,843 filed Mar. 17, 1978 now abandoned which is a continuation of Ser. No. 804,998 filed June 9, 1977, now abandoned.

The present invention relates to pharmaceutical compositions. Clavulanic acid, which is the compound of the formula (I):

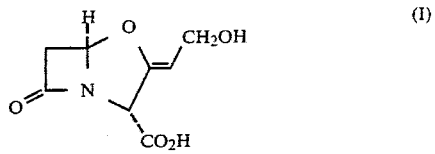

and its pharmaceutically acceptable salts are useful β-lactamase inhibitors (see for example Belgian Patent No. 827926). Clavulanic acid and its salts (referred to as synergists) are able to enhance the effectiveness of penicillins against many strains of pathogenic bacteria. It has now been discovered that when clavulanic acid or its salt is formulated with one of a certain group of penicillins then the resulting co-formulation has a particularly broad spectrum of activity.

Accordingly the present invention provides a pharmaceutical composition which comprises the compound of the formula (I) or a pharmaceutically acceptable salt thereof and a compound of the formula (II):

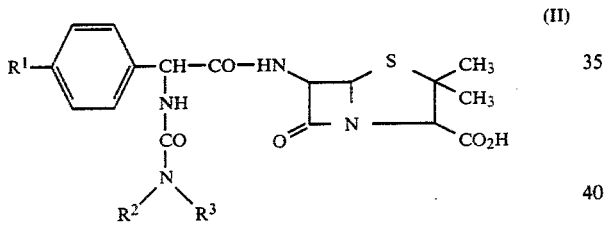

or a salt thereof wherein $R^1$ is a hydrogen atom or a hydroxyl or acetoxyl group, $R^2$ is a methyl group and $R^3$ is a $CO.R^4$ group wherein $R^4$ is a phenyl, iso-butyl, furyl, thienyl or $NHCH_3$ group or $R^2$ is joined to $R^3$ so that $NR^2R^3$ is an imidazolin-2-on-1-yl group.

Normally the compositions of this invention will be in a form suitable for parenteral administration.

Most suitably the compound of the formula (II) used in the composition of this invention is of the formula (III):

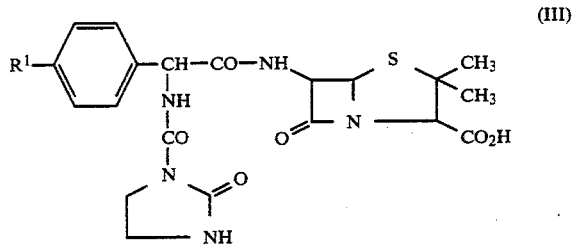

or a salt thereof wherein $R^1$ is as defined in relation to formula (II).

Most suitably $R^1$ is a hydrogen atom or a hydroxyl group. Preferably $R^1$ is a hydrogen atom. Normally the compounds of the formulae (I)–(III) will be present in the composition of this invention in the form of a pharmaceutically acceptable salt such as the sodium salt.

In general the compositions of this invention will contain the synergist and penicillin in the ratio of from 2:1 to 1:25. More suitably this ratio will be from 1:1 to 1:15 and preferably from 1:2 to 1.12, for example from 1:3 to 1:10.

The compositions of this invention may be presented as single or multi dose forms. In general single dose forms will contain from 62.5 mg to 2500 mg of the penicillin and from 25 mg to 250 mg of the synergist. These compositions may be administered once or more times per day so that for a 70 kg human the usual total daily dose of penicillin administered is from 250 mg to 5000 mg and the usual daily dose of synergist is from 100 mg to 1000 mg.

It is possible to prepare the compositions of this invention by conventional methods of mixing and formulating, for example as described in the aforementioned Belgian Patents. A particularly suitable form of the composition comprises a mixture of the synergist and the penicillin sealed into glass vials or bottles. Naturally the injectable compositions of this invention are rendered sterile.

The composition of this invention will be dissolvable in conventional solvents such as water for injection.

The following Example illustrates the invention:

EXAMPLE 1

Compounds (A) and (B):

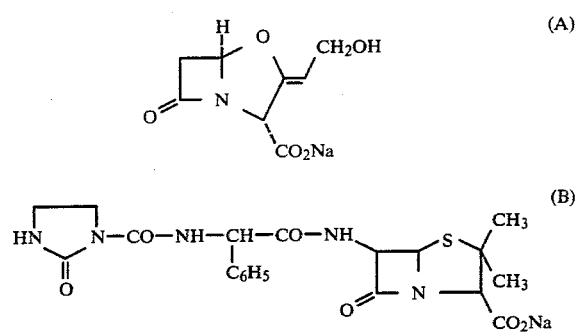

in sterile finely divided form may be filled into sterile glass vials in the following quantities:

| Compound (A) mg | Compound (B) mg |
| --- | --- |
| 25 | 62.5 |
| 25 | 125 |
| 25 | 250 |
| 25 | 500 |
| 50 | 250 |
| 50 | 500 |
| 100 | 1000 |
| 50 | 625 |

The compositions of Example 1 are effective in treating infections due to *Escherichia coli, Klebsiella aerogenes, Proteus mirabilis* and *Staphylococcus aureus.*

What we claim is:

1. An antibacterial mixture comprising a synergistically effective amount of the compound of the formula (I):

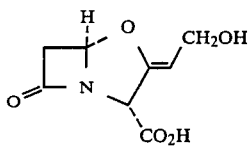 (I)

or a pharmaceutically acceptable salt thereof and an antibacterially effective amount of a compound of the formula (III):

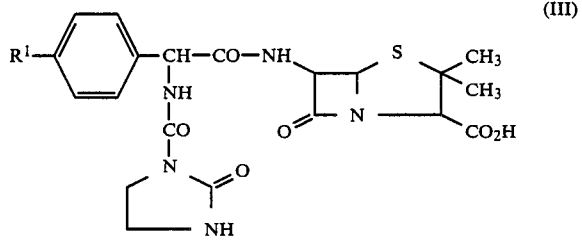 (III)

or a pharmaceutically acceptable salt thereof wherein $R^1$ is hydrogen or hydroxyl, in a weight ratio of from 1:1 to 1:15.

2. A mixture according to claim 1 wherein $R^1$ is hydroxyl.

3. A mixture according to claim 1 wherein the compounds of the formulae (I) and (III) or their salts are present in the ratio of from 1:1 to 1:15 by weight.

4. A mixture according to claim 1 wherein the compounds of the formulae (I) and (III) or their salts are present in the ratio of from 1:3 to 1:10 by weight.

5. A mixture according to claim 1 in unit dose form comprising from 25 to 250 mg of a salt of the compound of the formula (I) and from 62.5 to 2500 mg of a salt of the compound of the formula (III).

6. A mixture according to claim 1 wherein $R^1$ is hydrogen.

7. A mixture according to claim 1 wherein clavulanic acid is in the form of the sodium salt and the compound of the formula (III) is the sodium salt of the formula:

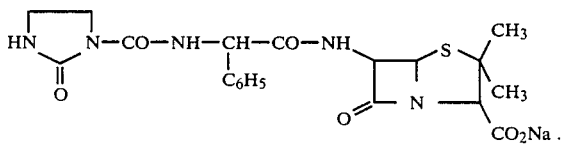

8. A mixture according to claim 1 wherein the compounds of the formulae (I) and (III) are in the form of pharmaceutically acceptable salts.

9. A mixture according to claim 8 wherein the compounds of the formulae (I) and (III) are in the form of their sodium salts.

10. A mixture according to claim 8 adapted for parenteral administration.

11. A pharmaceutical composition for treating bacterial infections in humans and animals which comprises a synergistically effective amount of clavulanic acid or a pharmaceutically acceptable salt thereof and an antibacterially effective amount of a compound of the formula (III):

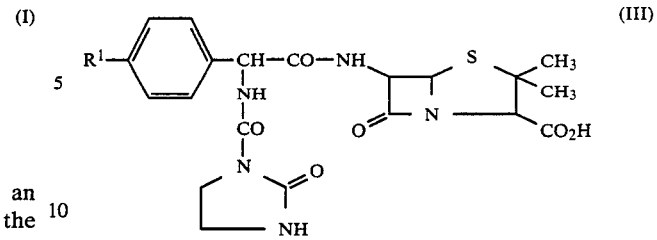 (III)

or a pharmaceutically acceptable salt thereof wherein $R^1$ is hydrogen or hydroxyl, in a weight ratio of 1:1 to 1:15, in combination with a pharmaceutically acceptable carrier.

12. A composition according to claim 4 wherein the weight ratio is 1:1 to 1:15.

13. A composition according to claim 11 wherein the weight ratio is 1:2 to 1:12.

14. A composition according to claim 11 wherein the weight ratio is 1:3 to 1:10.

15. A composition according to claim 11 wherein clavulanic acid and the compound of formula (III) are each in the form of a pharmaceutically acceptable salt.

16. A composition according to claim 11 wherein clavulanic acid is in the form of a pharmaceutically acceptable salt and the compound of formula (III) is in the form of the sodium salt.

17. A composition according to claim 11 wherein clavulanic acid and the compound of the formula (III) are each in the form of the sodium salt.

18. A composition according to claim 11 wherein $R^1$ is hydrogen.

19. A composition according to claim 11 wherein $R^1$ is hydroxyl.

20. A composition according to claim 11 in parenteral administration form.

21. A composition according to claim 11 wherein clavulanic acid is in the form of the sodium salt and the compound of the formula (III) is the sodium salt of the formula:

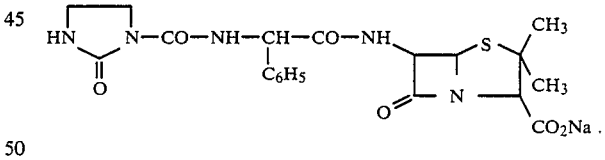

22. A method of treating bacterial infections in humans and animals which comprises parenterally administering to a human or animal in need thereof a synergistically effective amount of clavulanic acid or a pharmaceutically acceptable salt thereof and an antibacterially effective amount of a compound of the formula (III):

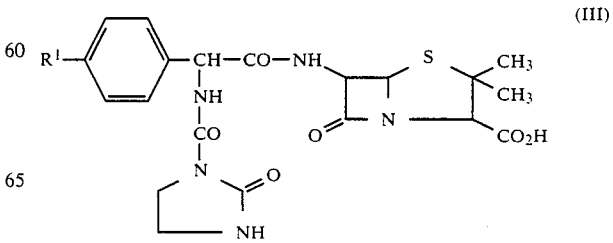 (III)

or a pharmaceutically acceptable salt thereof wherein $R^1$ is hydrogen or hydroxyl in a weight ratio of 1:1 to 1:15.

23. A method according to claim 22 wherein the weight ratio is 1:1 to 1:15.

24. A method according to claim 22 wherein the weight ratio is 1:2 to 1:12.

25. A method according to claim 22 wherein the weight ratio is 1:3 to 1:10.

26. A method according to claim 22 wherein the clavulanic acid and the compound of formula (III) are each in the form of a pharmaceutically acceptable salt.

27. A method according to claim 22 wherein clavulanic acid is in the form of a pharmaceutically acceptable salt and the compound of formula (III) is in the form of the sodium salt.

28. A method according to claim 22 wherein clavulanic acid and the compound of the formula (III) are each in the form of the sodium salt.

29. A method according to claim 22 wherein $R^1$ is hydrogen.

30. A method according to claim 22 wherein $R^1$ is hydroxyl.

31. A method according to claim 22 wherein clavulanic acid is in the form of the sodium salt and the compound of the formula (III) is the sodium salt of the formula:

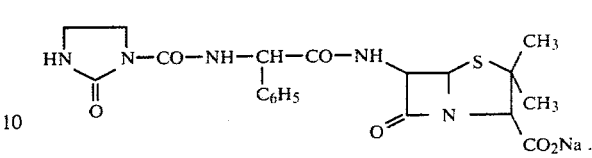

32. A composition according to claim 22 in unit dosage form wherein each dosage unit comprises 25 to 250 mg. of a pharmaceutically acceptable salt of clavulanic acid and from 6.25 to 2500 mg. of a pharmaceutically acceptable salt of the compound of formula (III).

33. A method of treating bacterial infections in humans and animals which comprises administering to said humans or animals an antibacterially effective amount of D-α-[(imidazolidin-2-oxo-1-yl)carbonylamino]-benzylpenicillin and clavulanic acid in a weight ratio of 1:1.

* * * * *